United States Patent
Bahn et al.

(10) Patent No.: US 10,101,338 B2
(45) Date of Patent: Oct. 16, 2018

(54) BIOMARKERS

(71) Applicants: Cambridge Enterprise Limited, Cambridgeshire (GB); Stichting VU, Amsterdam (NL)

(72) Inventors: Sabine Bahn, Cambridgeshire (GB); Emanuel Schwarz, Cambridgeshire (GB); Brenda Penninx, Amsterdam (NL); Nicole Vogelzangs, Amsterdam (NL)

(73) Assignees: Cambridge Enterprise Limited, Cambridge (GB); Stichting VU, Amsterdam (NL)

(*) Notice: Subject to any disclaimer, the term of this patent is extended or adjusted under 35 U.S.C. 154(b) by 0 days.

(21) Appl. No.: 14/570,076

(22) Filed: Dec. 15, 2014

(65) Prior Publication Data
US 2015/0099663 A1 Apr. 9, 2015

Related U.S. Application Data

(63) Continuation of application No. PCT/GB2013/051550, filed on Jun. 12, 2013.

(30) Foreign Application Priority Data

Jun. 14, 2012 (GB) .................................. 1210565.6

(51) Int. Cl.
| | | |
|---|---|---|
| A01N 37/18 | (2006.01) |
| G01N 33/53 | (2006.01) |
| G01N 33/68 | (2006.01) |
| G01N 33/573 | (2006.01) |

(52) U.S. Cl.
CPC ....... *G01N 33/6869* (2013.01); *G01N 33/573* (2013.01); *G01N 33/68* (2013.01); *G01N 33/6863* (2013.01); *G01N 33/6866* (2013.01); *G01N 2333/435* (2013.01); *G01N 2333/525* (2013.01); *G01N 2333/54* (2013.01); *G01N 2333/5403* (2013.01); *G01N 2333/5406* (2013.01); *G01N 2333/5409* (2013.01); *G01N 2333/5412* (2013.01); *G01N 2333/5418* (2013.01); *G01N 2333/5421* (2013.01); *G01N 2333/5428* (2013.01); *G01N 2333/55* (2013.01); *G01N 2333/555* (2013.01); *G01N 2333/57* (2013.01); *G01N 2333/96494* (2013.01); *G01N 2800/30* (2013.01); *G01N 2800/301* (2013.01)

(58) Field of Classification Search
None
See application file for complete search history.

(56) References Cited

U.S. PATENT DOCUMENTS

| | | |
|---|---|---|
| 6,420,108 B2 | 7/2002 | Mack et al. |
| 7,838,246 B2 | 11/2010 | Bahn et al. |
| 7,981,684 B2 | 7/2011 | Levin et al. |
| 8,158,374 B1 | 4/2012 | He et al. |
| 9,459,266 B2 | 10/2016 | Bahn et al. |
| 2006/0150264 A1 | 7/2006 | Bahn et al. |
| 2008/0220530 A1 | 9/2008 | Bahn et al. |
| 2009/0093430 A1 | 4/2009 | Lockstone et al. |
| 2009/0176257 A1 | 7/2009 | Bahn et al. |
| 2009/0286238 A1 | 11/2009 | Craddock et al. |
| 2010/0003694 A1 | 1/2010 | Bahn et al. |
| 2010/0129919 A1 | 5/2010 | Levin et al. |
| 2010/0291597 A1 | 11/2010 | Bahn et al. |
| 2011/0165554 A1 | 7/2011 | Levin et al. |
| 2012/0040852 A1 | 2/2012 | Levin et al. |
| 2012/0071339 A1 | 3/2012 | Bahn et al. |
| 2012/0071340 A1 | 3/2012 | Bahn et al. |
| 2012/0094858 A1 | 4/2012 | Bahn et al. |
| 2012/0251553 A1 | 10/2012 | Bahn et al. |
| 2013/0012402 A1 | 1/2013 | Bahn et al. |
| 2013/0017970 A1 | 1/2013 | Bahn et al. |
| 2013/0059750 A1 | 3/2013 | Bahn et al. |
| 2013/0078645 A1 | 3/2013 | Lundberg et al. |
| 2014/0200150 A1 | 7/2014 | Bahn et al. |
| 2014/0200151 A1 | 7/2014 | Bahn et al. |
| 2014/0271546 A1 | 9/2014 | Warf et al. |
| 2016/0116492 A1 | 4/2016 | Bahn et al. |

FOREIGN PATENT DOCUMENTS

| | | |
|---|---|---|
| WO | 2007/084734 | 7/2007 |
| WO | WO 2010/097631 A1 | 9/2010 |
| WO | WO 2011/121361 A1 | 10/2011 |
| WO | WO 2011/121362 A2 | 10/2011 |
| WO | WO 2011/144934 A1 | 11/2011 |
| WO | WO 2012/085555 A1 | 6/2012 |
| WO | WO 2012/085557 A2 | 6/2012 |
| WO | WO 2013/186562 A1 | 12/2013 |
| WO | 2014/184534 | 11/2014 |

OTHER PUBLICATIONS

Carvalho et al., "Cytokine profile in treatment-resistant depression", J. Psychopharmacology, vol. 24, Suppl. 3, p. A52, Abstract TB08 (2010).
Domenici et al., "Plasma protein biomarkers for depression and schizophrenia by multi analyte profiling of case-control collections", PLoS One, vol. 5, Issue 2, No. e9166, pp. 1-12 (2010).
International Search Report from PCT Patent Application No. PCT/GB2013/051550 dated Aug. 16, 2013, application now published as International Publication No. WO2013/186562 on Dec. 19, 2013.
Izmailov et al., "Algorithm development for diagnostic biomarker assays", Int. Rev. Neurobiology, vol. 101, pp. 279-298 (2011).
Lehto et al., "Serum chemokine levels in major depressive disorder", Psychoneuroendocrinology, vol. 35, No. 2, pp. 226-232 (2010).
Shen et al., "The plasma IL-18, MIP-1alpha, MCP-1, SDF-1 and rantes in patients with major depression", European Psychiatry, Editions Scientifiques et Medicales Elsevier, FR, vol. 23, p. S245 (2008).

(Continued)

*Primary Examiner* — Olga N Chernyshev
(74) *Attorney, Agent, or Firm* — Evan Law Group LLC

(57) ABSTRACT

The invention relates to biomarkers and a method of diagnosing or monitoring depression, anxiety disorder or other psychotic disorder.

23 Claims, 3 Drawing Sheets

(56) References Cited

OTHER PUBLICATIONS

Schwarz, E. et al., "Validation of a blood-based laboratory test to aid in the confirmation of a diagnosis of schizophrenia", Biomarker Insights, vol. 5, pp. 39-47, (2010).
Vogelzangs, N. et al., "Association of depressive disorders, depression characteristics and antidepressant medication with inflammation", Translation Psychiatry, vol. 2, pp. 1-9, (2012).
International Search Report and Written opinion dated Aug. 16, 2013 for PCT application number PCT/GB2013/051550.
Chan, M.K. et al., "Blood-based immune-endocrine biomarkers of treatment response in depression", Journal of Psychiatric Research, vol. 83, pp. 249-259, (2016).
Lamers, F. et al., "Serum proteomic profiles of depressive subtypes", Translational Psychiatry, vol. 6, pp 1-9, (2016).
Ruland, T. et al., "Molecular serum signature of treatment resistant depression", Psychopharmacology, vol. 233, pp. 3051-3059, (2016).
Vogelzangs, N. et al., "Cytokine production capacity in depression and anxiety", Translational Psychiatry, vol. 6, No. 5, pp. 1-9, (2016).
Ramsey, J.M. et al., "Sex differences in serum markers of major depressive disorder in the Netherlands study of depression and anxiety (NESDA)", PLoS One, vol. 11, No. 5, pp. 1-18, (2016).
Gottschalk, M.G. et al., "Serum biomarkers predictive of depressive episddies in panic disorder", Journal of Psychiatric Research, vol. 73, pp. 53-62, (2016).
Chan, M.K. et al., "Identification of an immune-neuroendocrine biomarker panel for detection of degression: A joint effects statistical approach", Neuroendocrinology, vol. 103, No. 6, pp. 693-710. (2016).
Bot, M. et al., "Serum proteomic profiling of major depressive disorder". Translational Psychiatry, vol. 5, pp. 1-9, (2015).
Gottschalk, M.G. et al., "Discovery of serum biomarkers predicting development of a subsequent depressive episode in social anxiety disorder", Brain, Behavior, and Immunity, vol. 48, pp. 123-131, (2015).
Gottschalk, M.G. et al., "Proteomic enrichment analysis of psychotic and affective disorders reveals common signatures in presynaptic glutamatergic signaling and energy metabolism", International Journal of Neuropsychopharmacology, pp. 1-11, (2015).
Wesseling, H. et al., "Targeted multiplexed selected reaction monitoring analysis evaluates protein expression changes of molecular risk factors for major psychiatric disorders", International Journal of Neuropsychopharmacology, pp. 1-13, (2014).
Stelzhammer, V. et al., "Distinct proteomic profiles in post-mortem pituitary glands from bipolar disorder and major depressive disorder patients", Journal of Psychiatric Research, vol. 60, pp. 40-48, (2015).
Stelzhammer, V. et al., "Proteomic changes in serum of first onset, antidepressant drug-naïve major depression patients", International Journal of Neuropsychopharmacology, vol. 17, pp. 1599-1608, (2014).
Shen, Y.D. et al., "The plasma IL-18, MIP-1α, MCP-1, SDF-1 and rantes in patients with majior depression", European Psychiatry, vol. 23, p. S245, Abstracts for Poster Session II, (2008).
Stelzhammer, V. et al., "Electroconvulsive therapy exerts mainly acute molecular changes in serum of major depressive disorder patients", European Neuropsychopharmacology, vol. 23, pp. 1199-1207, (2013).
Martins-de-Souza, D. et al., "Identification of proteomic signatures associated with depression and psychotic depression in postmortem brains from major depression patients", Translational Psychiatry, vol. 2, pp. 1-13, (2012).
International Preliminary Report on Patentability and written opinion dated Nov. 17, 2015 for PCT application No. PCT/GB2014/051457, 8 pages.
Perroud, N. et al., "Genome-wide association study of increasing suicidal ideation during antidepressant treatment in the GENDP project", The Pharmacogenomics Journal, vol. 12, pp. 68-77, (2012).
Jiang, L. et al., "Proteomic analysis of the cerebrospinal fluid of patients with schizophrenia", Amino Acids, vol. 25, issue 1, pp. 49-57, (2003).
Carboni, L. et al., "Early-life stress and antidepressants modulate peripheral biornarkers in a gene-environment rat model of depression", Progress in Neuro-Psychopharmacology & Biological Psychiatry, vol. 34, issue 6, pp. 1037-1048, (2010).
Woods, A.G. et al., "Potential biomarkers in psychiatry: focus on the cholesterol system", Journal of Cellular and Molecular Medicine, vol. 16, No. 6, pp. 1184-1195 (2012).
Choi, M-J. et al., "Brain-derived neurotrophic factor gene polymorphism (Val66Met) and citalopram response in major depressive disorder", Brain Research, vol. 1118, issue 1, pp. 176-182, (2006).
Anisman, H. et al., "Experiential and genetic contributions to depressive- and anxiety-like disorders: clinical and experimental studies", Neuroscience & Biobehavioral Reviews, vol. 32, issue 6, pp. 1185-1206, (2008).
Zhan, Y. et al., "Plasma-based proteomics reveals lipid metabolic and immunoregulatory dysregulation in post-stroke depression", European Psychiatry, vol. 29, issue 5, pp. 307-315, (2014).
Hamilton, M., "A rating scale for depression", Journal of Neurology, Neurosurgery & Psychiatry, vol. 23, pp. 56-62, (1960).
Setubal, J. et al., "Introduction to computational molecular biology", PWS Publishing Company, pp. 1-296, (1997).
International Search Report and written opinion dated Aug. 5, 2014 for PCT Application No. PCT/GB2014/051457.
Levin, Y. et al., "Multidimensional protein fractionation of blood proteins coupled to data-independent nanoLC-MS/MS analysis", Journal of Proteomics, vol. 73, pp. 689-695, (2010).
Levin, Y. et al., "Label-free LC-MS/MS quantitative proteomics for large-scale biomarker discovery in complex samples", Journal of Separation Science, vol. 30, pp. 2198-2203, (2007).
Krishnamurthy, D. et al., "Metabolic, hormonal and stress-related molecular changes in post-mortem pituitary glands from schizophrenia subjects", The World Journal of Biological Psychiatry, pp. 1-12, (2012).
Li, G-Z. et al., "Database searching and accounting of multiplexed precursor and product ion spectra from the data independent analysis of simple and complex peptide mixtures", Proteomics, vol. 9, pp. 1696-1719, (2009).
Stelzhammer, V. et al., "Analysis of the rat hypothalamus proteome by data-independent label-free LC-MS/MS", Proteomics, vol. 12, pp. 3386-3392, (2012).

BIOMARKERS

CROSS-REFERENCE TO RELATED APPLICATIONS

This application is a continuation of International Patent Application No. PCT/GB13/051550, filed Jun. 12, 2013, which claims the benefit of priority of GB Application No. 1210565.6, filed Jun. 14, 2012.

FIELD OF THE INVENTION

The invention relates to biomarkers and a method of diagnosing or monitoring depression, anxiety disorder or other psychotic disorder.

BACKGROUND OF THE INVENTION

Major depressive disorder is a mental disorder characterized by a pervasive low mood, low self-esteem, and loss of interest or pleasure in normally enjoyable activities. The term "major depressive disorder" (which is also known as clinical depression, major depression, unipolar depression, or unipolar disorder) was selected by the American Psychiatric Association for this symptom cluster under mood disorders in the 1980 version of the *Diagnostic and Statistical Manual of Mental Disorders* (DSM-III) classification, and has become widely used since.

The general term depression is often used to describe the disorder, but as it is also used to describe a depressed mood, more precise terminology can be used in clinical and research use. Major depression is a disabling condition which adversely affects a person's family, work or school life, sleeping and eating habits, and general health. In the United States, approximately 3.4% of people with major depression commit suicide, and up to 60% of all people who commit suicide have depression or another mood disorder.

The diagnosis of major depressive disorder is based on the patient's self-reported experiences, behaviour reported by relatives or friends, and a mental status exam. There is no laboratory test for depression, although physicians generally request tests for physical conditions that may cause similar symptoms. The most common time of onset is between the ages of 30 and 40 years, with a later peak between 50 and 60 years. Depression is reported about twice as frequently in women as in men, although men are at higher risk for suicide.

Most patients are treated in the community with antidepressant medication and some with psychotherapy or counseling. Hospitalization may be necessary in cases with associated self-neglect or a significant risk of harm to self or others.

A minority are treated with electroconvulsive therapy (ECT), under a short-acting general anaesthetic.

The course of the disorder varies widely, from one episode lasting months to a lifelong disorder with recurrent major depressive episodes. Depressed individuals have shorter life expectancies than those without depression, in part because of greater susceptibility to medical illnesses. Current and former patients may be stigmatized.

The understanding of the nature and causes of depression has evolved over the centuries, though many aspects of depression remain incompletely understood and are the subject of discussion and research.

Anxiety Disorder or Generalised Anxiety Disorder (GAD) is a disorder that causes sufferers to constantly feel anxious about a range of situations or issues. The term "anxiety" can relate to both physical and mental symptoms (such as physical tension and mental apprehension). Constant anxiety can often lead to patient's suffering from stress, loss of concentration and sleep deprivation.

Anxiety disorders are often comorbid with other mental disorders, particularly clinical depression i.e. major depressive disorder. There is therefore a need for a way of diagnosing these diseases in order to identify those in need of treatment.

Recent studies have indicated immune dysregulation in persons with depressive and anxiety disorders. By examining the expression of cytokines in response to ex vivo stimulation of blood by lipopolysaccharide (LPS), the innate production capacity of cytokines in depression and anxiety can be studied.

SUMMARY OF THE INVENTION

According to a first aspect of the invention, there is provided a use of one or more analytes selected from Interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor beta (TNF-β), Interleukin 4 (IL-4), Interferon gamma (IFN-γ) as a biomarker for depression, anxiety disorder or other psychotic disorder, or predisposition thereto.

According to a further aspect of the invention, there is provided the use of Interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor beta (TNF-β), Interleukin 4 (IL-4), Interferon gamma (IFN-γ) as a specific panel of analyte biomarkers for depression, anxiety disorder or other psychotic disorder, or predisposition thereto.

According to a further aspect of the invention, there is provided a method of diagnosing depression, anxiety disorder or other psychotic disorder, or predisposition in an individual thereto, comprising:
  (a) quantifying the amounts of the analyte biomarkers as defined herein in a biological sample obtained from an individual;
  (b) comparing the amounts of the analyte biomarkers in the biological sample with the amounts present in a normal control biological sample from a normal subject, such that a difference in the level of the analyte biomarkers in the biological sample is indicative of depression, anxiety disorder or other psychotic disorder, or predisposition thereto.

According to a further aspect of the invention, there is provided a method of monitoring efficacy of a therapy in a subject having, suspected of having, or of being predisposed to depression, anxiety disorder or other psychotic disorder, comprising detecting and/or quantifying, in a sample from said subject, the analyte biomarkers as defined herein.

A further aspect of the invention provides ligands, such as naturally occurring or chemically synthesised compounds, capable of specific binding to the peptide biomarker. A ligand according to the invention may comprise a peptide, an antibody or a fragment thereof, or an aptamer or oligonucleotide, capable of specific binding to the peptide biomarker. The antibody can be a monoclonal antibody or a fragment thereof capable of specific binding to the peptide biomarker. A ligand according to the invention may be labelled with a detectable marker, such as a luminescent, fluorescent or radioactive marker; alternatively or additionally a ligand according to the invention may be labelled with an affinity tag, e.g. a biotin, avidin, streptavidin or His (e.g. hexa-His) tag.

A biosensor according to the invention may comprise the peptide biomarker or a structural/shape mimic thereof capable of specific binding to an antibody against the peptide biomarker. There is also provided an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the peptide. In these uses, the detection and/or quantification can be performed on a biological sample such as from the group consisting of CSF, whole blood, blood serum, plasma, urine, saliva, or other bodily fluid, breath, e.g. as condensed breath, or an extract or purification therefrom, or dilution thereof.

Diagnostic or monitoring kits are provided for performing methods of the invention. Such kits will suitably comprise a ligand according to the invention, for detection and/or quantification of the peptide biomarker, and/or a biosensor, and/or an array as described herein, optionally together with instructions for use of the kit.

According to a further aspect of the invention, there is provided a kit for monitoring or diagnosing depression, anxiety disorder or other psychotic disorder, comprising a biosensor capable of detecting and/or quantifying the analyte biomarkers as defined herein.

Biomarkers for depression, anxiety disorder or other psychotic disorder are essential targets for discovery of novel targets and drug molecules that retard or halt progression of the disorder. As the level of the peptide biomarker is indicative of disorder and of drug response, the biomarker is useful for identification of novel therapeutic compounds in in vitro and/or in vivo assays. Biomarkers of the invention can be employed in methods for screening for compounds that modulate the activity of the peptide.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the peptide in a subject, comprising administering a test substance to a subject animal and detecting and/or quantifying the level of the peptide biomarker present in a test sample from the subject.

In general, when a doctor or other medical practitioner is apprised that a patient is suffering from anxiety disorder or depression, the practitioner will treat the individual to alleviate the causes or symptoms of the disorder. Thus, according to a further aspect of the invention, there is provided a method for treating anxiety disorder and a method for treating depression. Methods of treatment may comprise treating a patient with anxiolytic or antidepressant drugs and/or non-drug therapies. Treatment may be based upon a diagnosis or suspicion of anxiety disorder or depression derived from the methods, analyte biomarkers and specific panels of analyte biomarkers as described herein.

The results of any analyses according to the invention will often be communicated to physicians and/or patients (or other interested parties such as researchers) in a transmittable form that can be communicated or transmitted to any of the above parties. Therefore, according to a further aspect of the invention, there is provided systems for diagnosing and treating anxiety or depression. These systems may comprise sample analyzers, computers and software as described herein.

BRIEF DESCRIPTION OF THE FIGURES

Data has been based on logistic regression analyses and ANOVA, respectively, and has been adjusted for laboratory site, sex, age and years of education. High=highest quartile

Data has been based on logistic regression analyses and ANOVA, respectively, and has been adjusted for laboratory site, sex, age and years of education. High=highest quartile.

Figure 1:
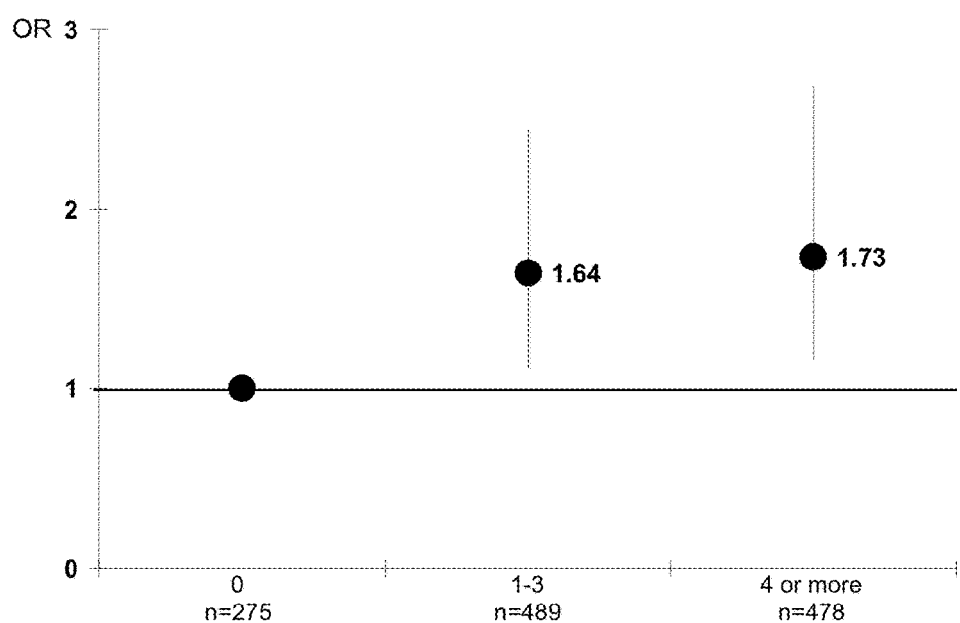
FIG. 1: Odds Ratio (OR) for presence of current depressive/anxiety disorder according to number of high LPS markers.
Figure 2:
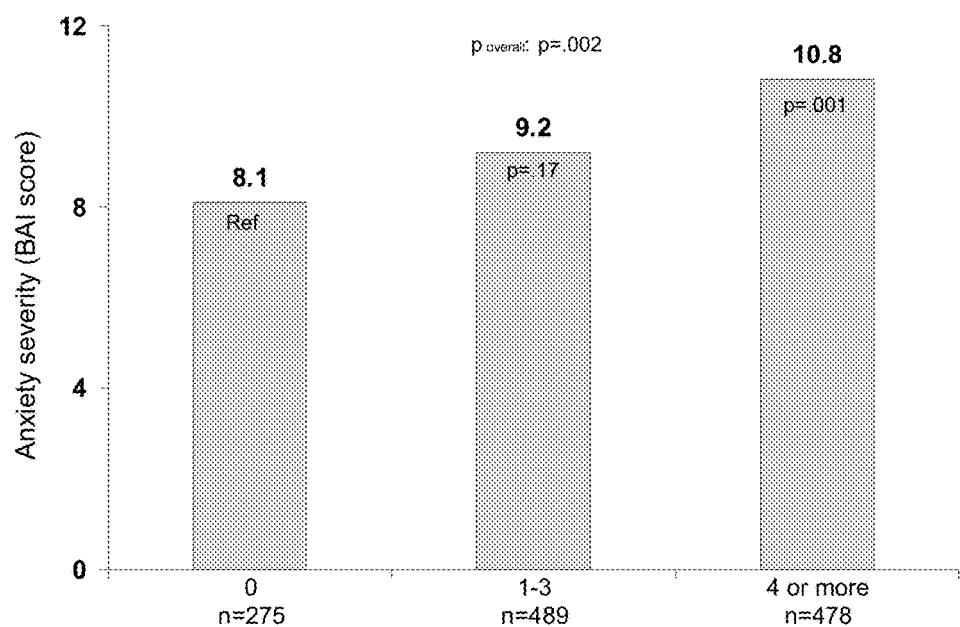
FIG. 2: Adjusted mean anxiety severity (BAI score) across number of high LPs markers.
Figure 3:
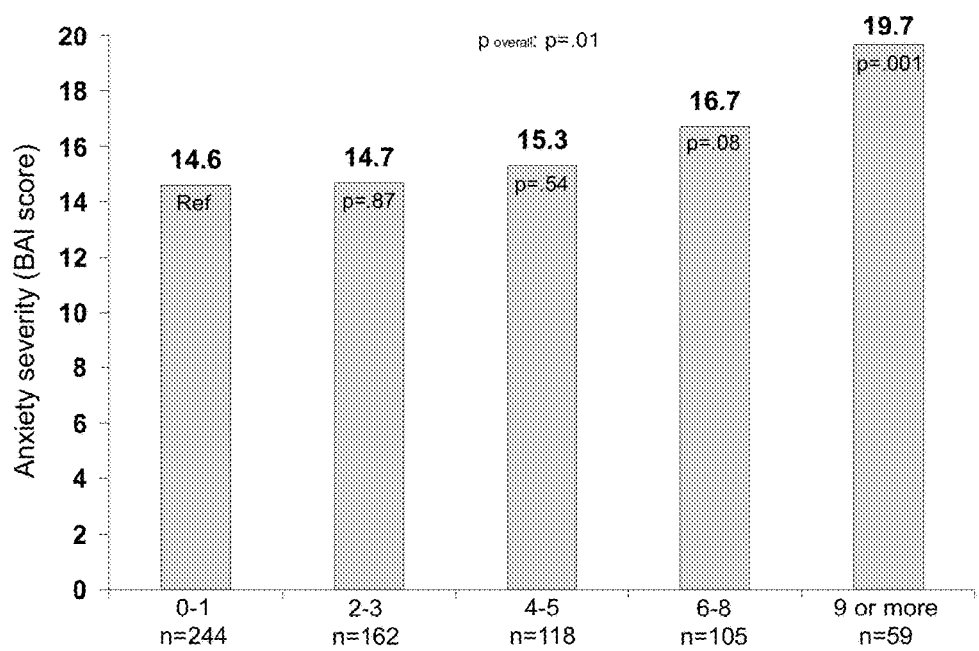

FIG. 3: Adjusted mean anxiety severity (BAI score) across number of high LPS markers within a subsample of persons with a current depressive/anxiety disorder.

Data has been adjusted for laboratory site, sex, age and years of education.

DETAILED DESCRIPTION OF THE INVENTION

According to a first aspect of the invention, there is provided a use of one or more analytes selected from Interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor beta (TNF-β), Interleukin 4 (IL-4), Interferon gamma (IFN-γ) as a biomarker for depression, anxiety disorder or other psychotic disorder, or predisposition thereto.

Data is provided herein which demonstrates that the analytes of the first aspect of the invention are statistically significant biomarkers for the diagnosis of depression and anxiety disorder. In particular, innate immune responsiveness is increased in persons with depressive and anxiety disorders, indicating a possible genetic vulnerability for depression or anxiety. Higher innate immune activity is also associated with higher symptom severity.

References herein to "depression" also include patients with "major depressive disorder" and "dysthymia". References herein to "anxiety disorder" also includes patients with "generalised anxiety disorder", "social phobia", "panic disorder" and "agrophobia".

In one embodiment, the analytes are selected from Interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor beta (TNF-β), Interleukin 4 (IL-4) and Interferon gamma (IFN-γ). The analytes of this embodiment relate to the LPS-stimulated inflammatory markers identified in the studies described herein.

In one embodiment, the analytes are selected from Interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2) and Tumor Necrosis Factor beta (TNF-β). The analytes of this embodiment relate to the markers analysed in the LPS-stimulated plasma samples as described in Table 2 herein.

According to a further aspect of the invention, there is provided the use of Interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor beta (TNF-β), Interleukin 4 (IL-4), Interferon gamma (IFN-γ) as a specific panel of analyte biomarkers for depression, anxiety disorder or other psychotic disorder, or predisposition thereto.

In one embodiment, the use of any of the aforementioned embodiments or aspects of the invention additionally comprises the use of one or more analytes selected from CRP, Interleukin 6 (IL-6) and Tumor Necrosis Factor alpha (TNF-α). The analytes of this embodiment relate to the circulating inflammatory markers identified in the studies described herein and have previously been studied association with depressive disorders, depression characteristics and to antidepressant medication with inflammation (Vogelzangs et al (2012) Transl Psychiatry 2, e79).

Thus, according to a further aspect of the invention there is provided the use of Interleukin 10 (IL-10), Interleukin 18 (IL-18), Interleukin 2 (IL-2), Interleukin 6 (IL-6), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor alpha (TNF-α), Tumor Necrosis Factor beta (TNF-β), CRP, Interleukin 4 (IL-4), Interferon gamma (IFN-γ) as a specific panel of analyte biomarkers for depression, anxiety disorder or other psychotic disorder, or predisposition thereto.

Data is provided herein which demonstrates that this specific panel of analyte biomarkers contained statistically significant biomarkers for the diagnosis of depression and anxiety disorder.

According to a further aspect of the invention, there is provided a method of diagnosing depression, anxiety disorder or other psychotic disorder, or predisposition in an individual thereto, comprising:
  (a) quantifying the amounts of the analyte biomarkers as defined herein in a biological sample obtained from an individual;
  (b) comparing the amounts of the analyte biomarkers in the biological sample with the amounts present in a normal control biological sample from a normal subject, such that a difference in the level of the analyte biomarkers in the biological sample is indicative of depression, anxiety disorder or other psychotic disorder, or predisposition thereto.

The term "biomarker" means a distinctive biological or biologically derived indicator of a process, event, or condition. Peptide biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

As used herein, the term "biosensor" means anything capable of detecting the presence of the biomarker. Examples of biosensors are described herein.

References herein to "other psychotic disorder" relate to any appropriate psychotic disorder according to DSM-IV Diagnostic and Statistical Manual of Mental Disorders, 4th edition, American Psychiatric Assoc, Washington, D.C., 2000. In one particular embodiment, the other psychotic disorder is a psychotic disorder related to schizophrenia. Examples of psychotic disorders related to schizophrenia include brief psychotic disorder delusional disorder, psychotic disorder due to a general medical condition, schizoeffective disorder, schizophreniform disorder, and substance-induced psychotic disorder.

In one embodiment, one or more of the biomarkers defined hereinbefore may be replaced by a molecule, or a measurable fragment of the molecule, found upstream or downstream of the biomarker in a biological pathway.

Biosensors according to the invention may comprise a ligand or ligands, as described herein, capable of specific binding to the peptide biomarker. Such biosensors are useful in detecting and/or quantifying a peptide of the invention.

Diagnostic kits for the diagnosis and monitoring of depression, anxiety disorder or other psychotic disorder are described herein. In one embodiment, the kits additionally contain a biosensor capable of detecting and/or quantifying a peptide biomarker.

Monitoring methods of the invention can be used to monitor onset, progression, stabilisation, amelioration and/or remission.

In methods of diagnosing or monitoring according to the invention, detecting and/or quantifying the peptide biomarker in a biological sample from a test subject may be performed on two or more occasions. Comparisons may be made between the level of biomarker in samples taken on two or more occasions. Assessment of any change in the level of the peptide biomarker in samples taken on two or more occasions may be performed. Modulation of the peptide biomarker level is useful as an indicator of the state of depression, anxiety disorder or other psychotic disorder or predisposition thereto. An increase in the level of the biomarker, over time is indicative of onset or progression, i.e. worsening of this disorder, whereas a decrease in the level of the peptide biomarker indicates amelioration or remission of the disorder, or vice versa.

A method of diagnosis of or monitoring according to the invention may comprise quantifying the peptide biomarker in a test biological sample from a test subject and comparing the level of the peptide present in said test sample with one or more controls.

The control used in a method of the invention can be one or more control(s) selected from the group consisting of: the level of biomarker peptide found in a normal control sample from a normal subject, a normal biomarker peptide level; a normal biomarker peptide range, the level in a sample from a subject with schizophrenia or other psychotic disorder, or a diagnosed predisposition thereto; schizophrenia or other psychotic disorder biomarker peptide level, or schizophrenia or other psychotic disorder biomarker peptide range.

In one embodiment, there is provided a method of diagnosing depression, anxiety disorder or other psychotic disorder, or predisposition thereto, which comprises:
  (a) quantifying the amount of the peptide biomarker in a test biological sample; and
  (b) comparing the amount of said peptide in said test sample with the amount present in a normal control biological sample from a normal subject.

For biomarkers which are increased in patients with depression, anxiety disorder or other psychotic disorder, a higher level of the peptide biomarker in the test sample relative to the level in the normal control is indicative of the presence of schizophrenia or other psychotic disorder, or predisposition thereto; an equivalent or lower level of the peptide in the test sample relative to the normal control is indicative of absence of depression, anxiety disorder or other psychotic disorder and/or absence of a predisposition thereto.

For biomarkers which are decreased in patients with depression, anxiety disorder or other psychotic disorder, a lower level of the peptide biomarker in the test sample relative to the level in the normal control is indicative of the presence of schizophrenia or other psychotic disorder, or predisposition thereto; an equivalent or lower level of the peptide in the test sample relative to the normal control is indicative of absence of depression, anxiety disorder or other psychotic disorder and/or absence of a predisposition thereto.

The term "diagnosis" as used herein encompasses identification, confirmation, and/or characterisation of depression, anxiety disorder or other psychotic disorder, or predisposition thereto. By predisposition it is meant that a subject does not currently present with the disorder, but is liable to be affected by the disorder in time. Methods of monitoring and of diagnosis according to the invention are useful to confirm the existence of a disorder, or predisposition thereto; to monitor development of the disorder by assessing onset and progression, or to assess amelioration or regression of the disorder. Methods of monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), reducing "down-time" and relapse rates.

Also provided is a method of monitoring efficacy of a therapy for depression, anxiety disorder or other psychotic disorder in a subject having such a disorder, suspected of having such a disorder, or of being predisposed thereto, comprising detecting and/or quantifying the peptide present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the level of the biomarker(s) in test samples taken on different occasions.

The invention provides a method for monitoring efficacy of therapy for depression, anxiety disorder or other psychotic disorder in a subject, comprising:

(a) quantifying the amount of the peptide biomarker; and
(b) comparing the amount of said peptide in said test sample with the amount present in one or more control(s) and/or one or more previous test sample(s) taken at an earlier time from the same test subject.

For biomarkers which are increased in patients with depression, anxiety disorder or other psychotic disorder, a decrease in the level of the peptide biomarker in the test sample relative to the level in a previous test sample taken earlier from the same test subject is indicative of a beneficial effect, e.g. stabilisation or improvement, of said therapy on the disorder, suspected disorder or predisposition thereto. For biomarkers which are decreased in patients with depression, anxiety disorder or other psychotic disorder, an increase in the level of the peptide biomarker in the test sample relative to the level in a previous test sample taken earlier from the same test subject is indicative of a beneficial effect, e.g. stabilisation or improvement, of said therapy on the disorder, suspected disorder or predisposition thereto.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following therapy. Samples can be taken at intervals over the remaining life, or a part thereof, of a subject.

The term "detecting" as used herein means confirming the presence of the peptide biomarker present in the sample. Quantifying the amount of the biomarker present in a sample may include determining the concentration of the peptide biomarker present in the sample. Detecting and/or quantifying may be performed directly on the sample, or indirectly on an extract therefrom, or on a dilution thereof.

In alternative aspects of the invention, the presence of the peptide biomarker is assessed by detecting and/or quantifying antibody or fragments thereof capable of specific binding to the biomarker that are generated by the subject's body in response to the peptide and thus are present in a biological sample from a subject having depression, anxiety disorder or other psychotic disorder or a predisposition thereto.

Detecting and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the peptide biomarker in the sample or samples. Biological samples that may be tested in a method of the invention include cerebrospinal fluid (CSF), whole blood, blood serum, plasma, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample of cerebrospinal fluid (CSF) by SELDI-TOF or MALDI-TOF to detect the presence or level of the peptide biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the peptide biomarkers may be performed using an immunological method, involving an antibody, or a fragment thereof capable of specific binding to the peptide biomarker. Suitable immunological methods include sandwich immunoassays, such as sandwich ELISA, in which the detection of the peptide biomarkers is performed using two antibodies which recognize different epitopes on a peptide biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes that are too small to precipitate. However, these complexes will scatter incident light and this can be measured using a nephelometer. The antigen, i.e. biomarker, concentration can be determined within minutes of the reaction.

Radioimmunoassay (RIA) methods employ radioactive isotopes such as $I^{125}$ to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radioimmunoassays (RIA). These methods use an enzyme to label either the antibody or target antigen. The sensitivity of ETA approaches that for RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of peptide biomarkers of the invention.

The Biotin-Avidin or Biotin-Streptavidin systems are generic labelling systems that can be adapted for use in immunological methods of the invention. One binding partner (hapten, antigen, ligand, aptamer, antibody, enzyme etc) is labelled with biotin and the other partner (surface, e.g. well, bead, sensor etc) is labelled with avidin or streptavidin. This is conventional technology for immunoassays, gene probe assays and (bio)sensors, but is an indirect immobilisation route rather than a direct one. For example a biotinylated ligand (e.g. antibody or aptamer) specific for a peptide biomarker of the invention may be immobilised on an avidin or streptavidin surface, the immobilised ligand may then be exposed to a sample containing or suspected of containing the peptide biomarker in order to detect and/or quantify a peptide biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, Fab fragments and F(ab')$_2$ fragments, fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers appropriate diagnostic tools such as biosensors can be developed, accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

Thus, according to a further aspect of the invention there is provided an apparatus for diagnosing or monitoring depression, anxiety disorder or other psychotic disorder which comprises a biosensor, microanalytical, microengineered, microseparation and/or immunochromatography system configured to detect and/or quantify any of the biomarkers defined herein.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the one or more biomarkers of the invention.

Methods involving detection and/or quantification of one or more peptide biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

The test substance can be a known chemical or pharmaceutical substance, such as, but not limited to, an antipsychotic disorder therapeutic; or the test substance can be novel synthetic or natural chemical entity, or a combination of two or more of the aforesaid substances.

There is provided a method of identifying a substance capable of promoting or suppressing the generation of the peptide biomarker in a subject, comprising exposing a test cell to a test substance and monitoring the level of the peptide biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

In methods for identifying substances of potential therapeutic use, non-human animals or cells can be used that are capable of expressing the peptide.

Screening methods also encompass a method of identifying a ligand capable of binding to the peptide biomarker according to the invention, comprising incubating a test substance in the presence of the peptide biomarker in conditions appropriate for binding, and detecting and/or quantifying binding of the peptide to said test substance.

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, which may be capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of the peptide biomarker, or of suppressing generation of the peptide biomarker.

The term "substances" includes substances that do not directly bind the peptide biomarker and directly modulate a function, but instead indirectly modulate a function of the peptide biomarker. Ligands are also included in the term substances; ligands of the invention (e.g. a natural or synthetic chemical compound, peptide, aptamer, oligonucleotide, antibody or antibody fragment) are capable of binding, suitably specific binding, to the peptide.

The invention further provides a substance according to the invention for use in the treatment of depression, anxiety disorder or other psychotic disorder, or predisposition thereto.

Also provided is the use of a substance according to the invention in the treatment of depression, anxiety disorder or other psychotic disorder, or predisposition thereto.

Also provided is the use of a substance according to the invention as a medicament.

A kit for diagnosing or monitoring depression, anxiety disorder or other psychotic disorder, or predisposition thereto is provided. Suitably a kit according to the invention may contain one or more components selected from the group: a ligand specific for the peptide biomarker or a structural/shape mimic of the peptide biomarker, one or more controls, one or more reagents and one or more consumables; optionally together with instructions for use of the kit in accordance with any of the methods defined herein.

The identification of biomarkers for depression, anxiety disorder or other psychotic disorder permits integration of diagnostic procedures and therapeutic regimes. Currently there are significant delays in determining effective treatment and hitherto it has not been possible to perform rapid assessment of drug response. Traditionally, many anti-psychotic therapies have required treatment trials lasting weeks to months for a given therapeutic approach. Detection of a peptide biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, in a time frame and with precision, not achievable using the current subjective measures.

Furthermore, diagnostic biomarker tests are useful to identify family members or patients at high risk of developing depression, anxiety disorder or other psychotic disorder. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder, poor patient compliance or substance abuse. If pharmacological treatment is assessed to be inadequate, then therapy can be reinstated or increased; a change in therapy can be given if appropriate. As the biomarkers are sensitive to the state of the disorder, they provide an indication of the impact of drug therapy or of substance abuse.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. The reference standard used for any embodiment disclosed herein may comprise average, mean, or median levels of the one or more analyte biomarkers or the levels of the specific panel of analyte biomarkers in a control population. The reference standard may additionally comprise cutoff values or any other statistical attribute of the control population, such as a standard deviation from the mean levels of the one or more analyte biomarkers or the levels of the specific panel of analyte biomarkers.

In some embodiments, comparing the level of the one or more analyte biomarkers is performed using a cutoff value. In related embodiments, if the level of the one or more analyte biomarkers is greater than the cutoff value, the individual may be diagnosed as having, or being at risk of developing depression or anxiety disorder. In other distinct embodiments, if the level of the one or more analyte biomarkers is less than the cutoff value, the individual may be diagnosed as having, or being at risk of developing depression or anxiety disorder. Cutoff values may be determined by statistical analysis of the control population to determine which levels represent a high likelihood that an individual does or does not belong to the control population. In some embodiments, comparing the level of the one or more analyte biomarkers is performed using other statistical methods. In related embodiments, comparing comprises logistic or linear regression. In other embodiments, comparing comprises computing an odds ratio.

In some embodiments, the control population may comprise healthy individuals, individuals with anxiety disorder, individuals with depression, or a mixed population of individuals with anxiety disorder, depression or both.

In some embodiments, individuals with levels of one or more analyte biomarkers or levels of a specific panel of analyte biomarkers greater than the reference levels would be more likely to have depression or anxiety. Therefore, an individual presenting with levels of the one or more analyte biomarkers or levels of the specific panel of analyte biomarkers greater than the reference standard would be a candidate for treatment with antidepressant or anxiolytic therapy, or with more aggressive therapy. On the other hand, an individual presenting with levels of the one or more analyte biomarkers or levels of the specific panel of analyte biomarkers less than or equal to the reference standard would be less likely to have depression and therefore be a candidate for no antidepressant or anxiolytic therapy, delayed antidepressant or anxiolytic therapy or less aggressive antidepressant or anxiolytic therapy.

In other embodiments, individuals with levels of one or more analyte biomarkers or levels of a specific panel of analyte biomarkers less than the reference levels would be more likely to have depression or anxiety. Therefore, an individual presenting with levels of the one or more analyte biomarkers or levels of the specific panel of analyte biomarkers less than the reference standard would be a candidate for treatment with antidepressant or anxiolytic therapy, or with more aggressive therapy. On the other hand, an individual presenting with levels of the one or more analyte biomarkers or levels of the specific panel of analyte biomarkers greater than or equal to the reference standard would be less likely to have depression and therefore be a candidate for no antidepressant or anxiolytic therapy, delayed antidepressant or anxiolytic therapy or less aggressive antidepressant or anxiolytic therapy.

Reference Therapy for Treatment

In some embodiments, a patient is treated more or less aggressively than a reference therapy. A reference therapy is any therapy that is the standard of care for anxiety disorder or depression. The standard of care can vary temporally and geographically, and a skilled person can easily determine the appropriate standard of care by consulting the relevant medical literature.

In some embodiments, based on a determination that levels of a panel of biomarkers is a) greater than, b) less than, c) equal to, d) greater than or equal to, or e) less than or equal to a reference standard, treatment will be either 1) more aggressive, or 2) less aggressive than a standard therapy.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Anxiety Disorder

Health practitioners treat anxiety disorder by taking actions to ameliorate the causes or symptoms of the disorder in a patient. Treatment may comprise drug-based or non-drug-based therapies.

Drug-based therapies may include: selecting and administering one or more anxiolytic drugs to the patient, adjusting the dosage of an anxiolytic drug, adjusting the dosing schedule of an anxiolytic drug, and adjusting the length of the therapy with an anxiolytic drug. Anxiolytic drugs are selected by practitioners based on the nature of the symptoms and the patient's response to any previous treatments. The dosage of an anxiolytic drug can be adjusted as well by the practitioner based on the nature of the drug, the nature of the patient's symptoms, the patient's response to previous treatment, and the patient's response to the drug. The dosing schedule can also be adjusted by the practitioner based on the nature of the drug, the nature of the patient's symptoms, the patient's response to previous treatment, and the patient's response to the drug. Also, the length of the therapy can be adjusted by the practitioner based on the nature of the drug, the nature of the patient's symptoms, the patient's response to previous treatment, and the patient's response to the drug. Additionally, the practitioner can select between a single drug therapy, a dual drug therapy, or a triple drug therapy. In some embodiments, a practitioner may optionally treat the patient with a combination of one or more anxiolytic drugs and one or more non-drug-based therapies.

In one embodiment, the practitioner begins anxiolytic therapy based on a comparison between a reference level and the levels of one or more analyte biomarkers or the levels of a specific panel of analyte biomarkers in a sample from a patient. In one embodiment, therapy comprises the selection and administration of an anxiolytic drug to the patient by the practitioner. In another embodiment, therapy comprises the selection and administration of two anxiolytic drugs to the patient by the practitioner as part of dual therapy. In another embodiment, therapy comprises the selection and administration of three anxiolytic drugs to the patient by the practitioner as part of triple therapy.

Anxiolytic drugs are commonly used by medical practitioners, and a skilled person may identify the appropriate anxiolytic drug to administer based on the medical literature. In some embodiments, treatment comprises administering to an individual a selective serotonin reuptake inhibitor ("SSRI"). In some embodiments, the SSRI is citalopram. In some embodiments, the SSRI is escitalopram. In some embodiments, the SSRI is fluoxetine. In some embodiments, the SSRI is paroxetine. In some embodiments, the SSRI is sertraline.

In other embodiments, treatment comprises administering to an individual a serotonin-norepinephrine reuptake inhibitors ("SNRI"). In some embodiments, the SNRI is venlafaxine. In other embodiments, the SNRI is duloxetine.

In other embodiments, treatment comprises administering to an individual a benzodiazepine drug. In some embodiments, the benzodiazepine is alprazolam. In some embodiments, the benzodiazepine is clonazepam. In some embodiments, the benzodiazepine is diazepam. In some embodiments, the benzodiazepine is lorazepam.

In other embodiments, treatment comprises administering to an individual a tricyclic antidepressant ("tricyclic"). In some embodiments, the tricyclic is amitriptyline. In some embodiments, the tricyclic is imipramine. In some embodiments, the tricyclic is nortriptyline.

In addition to or in lieu of drug-based therapies, in some embodiments a practitioner may also treat an individual with non-drug based anxiolytic therapies. In some embodiments, the non-drug based therapy comprises cognitive-behavioral therapy. In some embodiments, the non-drug based therapy comprises exposure therapy. In some embodiments, the non-drug based therapy comprises acceptance and commitment therapy. In some embodiments, the non-drug based therapy comprises dialectical behavioral therapy. In some embodiments, the non-drug based therapy comprises interpersonal therapy. In some embodiments, the non-drug based therapy comprises eye movement desensitization and reprocessing.

In one embodiment, the practitioner adjusts the anxiolytic therapy based on a comparison between a reference level and the levels of one or more analyte biomarkers or the levels of a specific panel of analyte biomarkers in a sample from a patient. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. In one embodiment a less aggressive therapy comprises delaying treatment. In one embodiment a less aggressive therapy comprises selecting and administering less potent drugs. In one embodiment a less aggressive therapy comprises decreasing dosage of anxiolytic drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises earlier administration of anxiolytic drugs. In one embodiment a more aggressive therapy comprises increased dosage of anxiolytic drugs. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Treatment of Depression

Health practitioners treat depression by taking actions to ameliorate the causes or symptoms of the disorder in a patient. Treatment may comprise drug-based or non-drug-based therapies.

Drug-based therapies may include: selecting and administering one or more antidepressant drugs to the patient, adjusting the dosage of an antidepressant drug, adjusting the dosing schedule of an antidepressant drug, and adjusting the length of the therapy with an antidepressant drug. Antidepressant drugs are selected by practitioners based on the nature of the symptoms and the patient's response to any previous treatments. The dosage of an antidepressant drug can be adjusted as well by the practitioner based on the nature of the drug, the nature of the patient's symptoms, the patient's response to previous treatment, and the patient's response to the drug. The dosing schedule can also be adjusted by the practitioner based on the nature of the drug, the nature of the patient's symptoms, the patient's response to previous treatment, and the patient's response to the drug. Also, the length of the therapy can be adjusted by the practitioner based on the nature of the drug, the nature of the patient's symptoms, the patient's response to previous treatment, and the patient's response to the drug. Additionally, the practitioner can select between a single drug therapy, a dual drug therapy, or a triple drug therapy. In some embodiments, a practitioner may optionally treat the patient with a combination of one or more antidepressant drugs and one or more non-drug-based therapies.

In one embodiment, the practitioner begins antidepressant therapy based on a comparison between a reference level and the levels of one or more analyte biomarkers or the levels of a specific panel of analyte biomarkers in a sample from a patient. In one embodiment, therapy comprises the selection and administration of an antidepressant drug to the patient by the practitioner. In another embodiment, therapy comprises the selection and administration of two antidepressant drugs to the patient by the practitioner as part of dual therapy. In another embodiment, therapy comprises the selection and administration of three antidepressant drugs to the patient by the practitioner as part of triple therapy.

Antidepressant drugs are commonly used by medical practitioners, and a skilled person may identify the appropriate antidepressant drug to administer based on the medical literature. In some embodiments, treatment comprises administering to an individual a selective serotonin reuptake inhibitor ("SSRI"). In some embodiments, the SSRI is citalopram. In some embodiments, the SSRI is escitalopram. In some embodiments, the SSRI is fluoxetine. In some embodiments, the SSRI is paroxetine. In some embodiments, the SSRI is sertraline.

In other embodiments, treatment comprises administering to an individual a serotonin-norepinephrine reuptake inhibitors ("SNRI"). In some embodiments, the SNRI is venlafaxine. In other embodiments, the SNRI is duloxetine.

In other embodiments, treatment comprises administering to an individual a norepinephrine and dopamine reuptake inhibitor ("NDRI"). In one embodiment, the NDRI is bupropion.

In other embodiments, treatment comprises administering to an individual a tetracyclic antidepressant ("tetracyclic"). In some embodiments, the tetracyclic is amoxapine. In some embodiments, the tetracyclic is maprotiline. In some embodiments, the tetracyclic is mazindol. In some embodiments, the tetracyclic is mirtazapine.

In other embodiments, treatment comprises administering to an individual a tricyclic antidepressant ("tricyclic"). In some embodiments, the tricyclic is amitriptyline. In some embodiments, the tricyclic is imipramine. In some embodiments, the tricyclic is nortriptyline.

In other embodiments, treatment comprises administering to an individual a monoamine oxidase inhibitor ("MAOI"). In some embodiments, the MAOI is selegiline. In some embodiments, the MAOI is isocarboxazid. In some embodiments, the MAOI is phenelzine. In some embodiments, the MAOI is tranylcypromine.

In addition to or in lieu of drug-based therapies, in some embodiments a practitioner may also treat an individual with non-drug-based antidepressant therapies. In some embodiments, the non-drug based therapy comprises cognitive-behavioral therapy. In some embodiments, the non-drug based therapy comprises psychotherapy. In a related embodiment, the non-drug based therapy comprises psychodynamic therapy. In some embodiments, the non-drug based therapy comprises electroconvulsive therapy. In some embodiments, the non-drug based therapy comprises hospitalization and residential treatment programs. In some embodiments, the non-drug based therapy comprises vagus nerve stimulation. In some embodiments, the non-drug based therapy comprises transcranial magnetic stimulation. In some embodiments, the non-drug based therapy comprises regular, vigorous exercise.

In one embodiment, the practitioner adjusts the antidepressant therapy based on a comparison between a reference level and the levels of one or more analyte biomarkers or the levels of a specific panel of analyte biomarkers in a sample from a patient. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. In one embodiment a less aggressive therapy comprises delaying treatment. In one embodiment a less aggressive therapy comprises selecting and administering less potent drugs. In one embodiment a less aggressive therapy comprises decreasing dosage of antidepressant drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises earlier administration of antidepressant drugs. In one embodiment a more aggressive therapy comprises increased dosage of antidepressant drugs. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Systems for Diagnosing and Treating Anxiety or Depression

The results of any analyses according to the invention will often be communicated to physicians and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. The statements and visual forms can be recorded on a tangible medium such as papers, computer readable media such as hard disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on levels of one or more analyte biomarkers or levels of a specific panel of analyte biomarkers for at least one patient sample. The method comprises the steps of (1) determining levels of one or more analyte biomarkers or levels of a specific panel of analyte biomarkers for at least one patient sample according to methods of the present invention; and (2) embodying the result of the determining step in a transmittable form. The transmittable form is the product of such a method.

Techniques for analyzing levels of one or more analyte biomarkers or levels of a specific panel of analyte biomarkers for at least one patient sample will often be implemented using hardware, software or a combination thereof in one or more computer systems or other processing systems capable of effectuating such analysis.

Thus, the present invention further provides a system for determining whether an individual suffers from depression or anxiety disorder, comprising: (1) a sample analyzer for determining the levels of one or more analyte biomarkers or levels of a specific panel of analyte biomarkers for at least one patient sample, wherein the sample analyzer contains the patient sample; (2) a first computer program for (a) receiving data regarding the levels of one or more analyte biomarkers or the levels of a specific panel of analyte biomarkers; and optionally (3) a second computer program for comparing the test value to one or more reference standards each associated with a predetermined degree of risk of depression or anxiety.

The sample analyzer can be any instruments useful in determining the levels of biomarkers in a sample, as described herein.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft WINDOWS™ environment including WINDOWS® 98, WINDOWS® 2000, WINDOWS® NT operating systems, and the like. In addition, the application can also be written for the MACINTOSH®, SUN®, UNIX® or LINUX®, environment. In addition, the functional steps can also be implemented using a universal or platform-independent programming language. Examples of such multi-platform programming languages include, but are not limited to, hypertext markup language (HTML), JAVA®, JAVASCRIPT®, Flash programming language, common gateway interface/structured query language (CGI/SQL), practical extraction report language (PERL), APPLE-SCRIPT® and other system script languages, programming language/structured query language (PL/SQL), and the like, JAVA®-or JAVASCRIPT®-enabled browsers such as HotJava™, Microsoft™Explorer™, or Netscape™ can be used. When active content web pages are used, they may include JAVA® applets or ACTIVEX® controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out disease risk analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instructions which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Thus one aspect of the present invention provides a system for determining whether a patient has depression or anxiety disorder. Generally speaking, the system comprises (1) computer program for receiving, storing, and/or retrieving data regarding levels of biomarkers in a patient's sample and optionally clinical parameter data (e.g., disease-related symptoms); (2) computer program for querying this patient data; (3) computer program for concluding whether an individual suffers from depression or anxiety based on this patient data; and optionally (4) computer program for outputting/displaying this conclusion. In some embodiments this computer program for outputting the conclusion may comprise a computer program for informing a health care professional of the conclusion The practice of the present invention may also employ conventional biology methods, software and systems. Computer software products of the invention typically include computer readable media having computer-executable Instructions for performing the logic steps of the method of the invention. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, Ser. No. 61/793,031, Page 38 of 64 BIOINFORMATICS: A PRACTICAL GUIDE FOR ANALYSIS OF GENE AND PROTEINS (Wiley & Sons, Inc., 2nd ed., 2001); see also, U.S. Pat. No. 6,420,108.

The following study provides an example of the invention present herein.

Methods

Sample Cohort

Samples were collected as part of the Netherlands Study for Anxiety and Depression (NESDA). Plasma were taken from a total of 1153 subjects, including patients with a current diagnosis of depression and/or anxiety disorder, recovered subjects with a previous diagnosis of depression and/or anxiety disorder as well as controls recruited at the same geographic locations. All samples were stimulated by the addition of lipopolysaccharide (LPS).

TABLE 1

Demographic details of subjects

|  | Control | Recovered Depression/ Anxiety | Current Depression/ Anxiety |
| --- | --- | --- | --- |
| Number of Subjects | 278 | 224 | 651 |
| Site (Amsterdam, Groningen, Leiden) | 100/57/121 | 87/51/86 | 213/99/339 |
| Age | 42.1 ± 14.0 | 46.1 ± 12.2 | 42 ± 12.2 |
| Sex (m/f) | 107/171 | 73/151 | 213/438 |
| Education level (Basic/Intermed/High) | 6/142/130 | 10/103/111 | 56/416/179 |
| Becks Anxiety Inventory | 3.1 ± 4.1 | 17.1 ± 10.8 | 7.1 ± 6.6 |

Values are displayed as mean ± sd.

Multiplexed Immunoassay Measurements

Seventeen cytokines (Granulocyte-Macrophage CSF, Interferon gamma, Interleukin-10, Interleukin-18, Interleukin-2, Interleukin-3, Interleukin-4, Interleukin-5, Interleukin-6, Interleukin-7, Interleukin-8, Monocyte Chemotactic Protein 1, Macrophage Inflammatory Protein-1 alpha, Macrophage Inflammatory Protein-1 beta, Matrix Metalloproteinase-2, Tumor Necrosis Factor alpha and Tumor Necrosis Factor beta) were measured using the multiplex immunoassay platform Human CytokineMAP™ A 1.0) in a Clinical Laboratory Improvement Amendments-certified laboratory at Rules Based Medicine (Austin, Tex., USA) as described previously (Schwarz et al., 2010). Assays were calibrated and absolute protein concentrations determined using standards and performance was verified using quality control samples.

Data Analysis

Analytes with more than 60% missing values were excluded from further analysis. After this filtering step, 13 out of 17 analytes remained in the dataset. Values measured outside the limits of detection were replaced by the minimum or maximum value measured for a given analyte, respectively. Missing values due to insufficient quantity were replaced by the median measured value for a given molecule. Values were log 10-transformed and values outside 3.5 standard deviations of the mean were truncated to approximate normality of the measured concentrations. Analyte levels were compared between controls, subjects recovered from prior episodes of anxiety and/or depression and patients with acute depression and/or anxiety disorder using analysis of variance (ANOVA). Molecular levels were also compared against the total score of the Becks Anxiety Inventory to detect potential associations between plasma readouts and symptom severity. For this purpose, collection site, gender, age and education level were used as covariates in an analysis of covariance (ANCOVA). P-values below 0.05 were considered to indicate statistical significance.

Results

We found nine out of the 13 analytes that passed filtering to be significantly altered in the three group comparison including subjects with a current diagnosis of depression and/or anxiety disorder, recovered subjects with a previous diagnosis of depression and/or anxiety disorder as well as controls (P<0.05, Table 2). Ten of the 13 analytes were altered when comparing symptom severity scores as measured by the Becks Anxiety Inventory (BAI) against molecule levels after adjustment for potential confounding variables (Table 2).

TABLE 2

Summary of significant findings in LPS stimulated plasma samples.

| Analyte | Depression/Anxiety | | | Three group comparison p-value | BAI p-value |
|---|---|---|---|---|---|
| | Control | Recovered | Current | | |
| Interleukin 10 (IL-10) | 5.17 ± 0.97 | 5.21 ± 1.00 | 5.27 ± 0.90 | 0.347 | 0.004 |
| Interleukin 18 (IL-18) | 5.46 ± 0.34 | 5.49 ± 0.38 | 5.55 ± 0.33 | 0.001 | 0.001 |
| Interleukin 2 (IL-2) | 2.04 ± 0.54 | 2.05 ± 0.64 | 2.15 ± 0.59 | 0.018 | 0.151 |
| Interleukin 6 (IL-6) | 9.95 ± 0.82 | 9.89 ± 0.85 | 10.05 ± 0.72 | 0.018 | 0.010 |
| Interleukin 8 (IL-8) | 9.07 ± 0.68 | 9.2 ± 0.72 | 9.3 ± 0.60 | <0.001 | <0.001 |
| Monocyte Chemotactic Protein 1 (MCP-1) | 7.14 ± 0.70 | 7.16 ± 0.77 | 7.3 ± 0.66 | 0.002 | 0.002 |
| Macrophage Inflammatory Protein 1 alpha (MIP-1α) | 9.58 ± 0.81 | 9.57 ± 0.85 | 9.71 ± 0.69 | 0.020 | 0.002 |
| Macrophage Inflammatory Protein 1 beta (MIP-1β) | 12.2 ± 0.61 | 12.23 ± 0.63 | 12.3 ± 0.53 | 0.022 | 0.005 |
| Matrix Metalloproteinase 2 (MMP-2) | 4.19 ± 0.36 | 4.19 ± 0.39 | 4.25 ± 0.32 | 0.005 | 0.001 |
| Tumor Necrosis Factor alpha (TNF-α) | 7.85 ± 0.76 | 7.79 ± 0.77 | 7.86 ± 0.68 | 0.434 | 0.006 |
| Tumor Necrosis Factor beta (TNF-β) | 5.57 ± 0.59 | 5.53 ± 0.68 | 5.66 ± 0.55 | 0.004 | 0.008 |

Values are displayed as mean ± sd.

REFERENCES

Schwarz E, Izmailov R, Spain M, et al.: Validation of a blood-based laboratory test to aid in the confirmation of a diagnosis of schizophrenia. Biomark Insights 5:39-47, 2010.

The following study provides further support for the invention described herein.

Methods

Population

Persons (18-65 years; 66% women) with current (i.e. past 6-month; n=694) or remitted (n=251) DSM-IV depressive or anxiety disorders and healthy controls (n=297) of the Netherlands Study of Depression and Anxiety (NESDA).

Psychopathology

Depressive disorder (dysthymia, major depressive disorder) and anxiety disorder (generalized anxiety disorder, social phobia, panic disorder, agoraphobia) based on CIDI psychiatric interview.

Symptom Severity

Inventory of Depressive Symptoms (IDS), 0-84 Beck Anxiety Inventory (BAI), 0-63 LPS-stimulated inflammatory markers Using Multi-Analyte Profiling technology, plasma levels of 13 cytokines (interferon (IFN)-γ, interleukin (IL)-2, IL-4, IL-6, IL-8, IL-10, IL-18, monocyte chemotactic protein (MCP)-1, macrophage inflammatory protein (MIP)-1α, MIP-1β, matrix metalloproteinase (MMP)-2, tumor necrosis factor alpha and beta (TNF-α, TNF-β) were assayed after whole blood stimulation by addition of LPS.

TABLE 3

Baseline characteristics according to depressive/anxiety disorder status.

| | Healthy control N = 297 | Remitted depressive or anxiety disorder N = 251 | Current depressive or anxiety disorder N = 694 | p * |
|---|---|---|---|---|
| Sociodemographics and lifestyle characteristics | | | | |
| Women, % | 62.0 | 66.9 | 66.9 | .30 |
| Age (years), mean (SD) | 42.2 (13.9) | 45.9 (12.2) | 41.9 (12.1) | <.001 |
| Education (years), mean (SD) | 13.1 (3.2) | 12.8 (3.3) | 11.7 (3.2) | <.001 |
| Laboratory site | | | | .001 |
| Amsterdam, % | 39.1 | 45.8 | 38.6 | |
| Leiden, % | 41.4 | 33.9 | 47.4 | |
| Groningen, % | 15.8 | 16.7 | 9.7 | |
| Heerenveen, % | 3.7 | 3.6 | 4.3 | |
| Current smoker, % | 23.6 | 34.3 | 43.9 | <.001 |
| Body mass index, mean (SD) | 25.2 (4.7) | 26.2 (4.8) | 25.7 (5.2) | .06 |
| Depression and anxiety characteristics | | | | |
| Depression severity (IDS), mean (SD) | 7.2 (6.8) | 14.1 (9.3) | 29.3 (12.8) | <.001 |
| Anxiety severity (BAI), mean (SD) | 3.2 (4.4) | 7.3 (6.7) | 17.2 (10.8) | <.001 |
| Within current depressive/anxiety subsample (n = 694) | | | | |
| Depressive and/or anxiety disorder | | | | — |
| Depressive disorder only, % | — | — | 22.0 | |

TABLE 3-continued

Baseline characteristics according to depressive/anxiety disorder status.

| | Healthy control N = 297 | Remitted depressive or anxiety disorder N = 251 | Current depressive or anxiety disorder N = 694 | p * |
|---|---|---|---|---|
| Anxiety disorder only, % | — | — | 31.3 | |
| Depressive and anxiety disorder, % | — | — | 46.7 | |
| Duration of symptoms (%), mean (SD) | — | — | 54.4 (35.3) | — |
| Age of disorder onset (years), mean (SD) | — | — | 21.3 (12.5) | — |
| Antidepressant use | | | | — |
| No antidepressant, % | — | — | 62.0 | |
| SSRI, % | — | — | 24.9 | |
| SNRI, % | — | — | 5.9 | |
| TCA, % | — | — | 4.2 | |
| TeCA, % | — | — | 3.0 | |
| Circulating inflammatory markers | | | | |
| CRP (mg/l), median (IQR) § | 1.08 (0.51-2.37) | 1.35 (0.53-2.76) | 1.29 (0.58-3.34) | .05 |
| IL-6 (pg/ml), median (IQR) § | 0.71 (0.50-1.20) | 0.73 (0.47-1.23) | 0.84 (0.53-1.40) | .007 |
| TNF-α (pg/ml), median (IQR) § | 0.70 (0.60-1.10) | 0.80 (0.60-1.10) | 0.80 (0.60-1.10) | .52 |
| LPS-stimulated inflammatory markers | | | | |
| IFN-γ (pg/ml), median (IQR) § | 9.8 (6.5-15.7) | 9.3 (6.5-13.8) | 10.2 (7.2-14.5) | .10 |
| IL-2 (pg/ml), median (IQR) § | 8.0 (5.6-11.5) | 8.2 (5.5-12.2) | 9.2 (6.0-13.0) | .01 |
| IL-4 (pg/ml), median (IQR) § | 8.2 (4.0-13.4) | 8.6 (4.1-15.0) | 9.0 (4.2-15.0) | .08 |
| IL-6 (pg/ml), median (IQR) § | 25200 (15500-35800) | 24000 (15800-33000) | 26700 (17800-35250) | .04 |
| IL-8 (pg/ml), median (IQR) § | 9130 (5785-13400) | 10600 (6360-15800) | 10800 (7530-15900) | <.001 |
| IL-10 (pg/ml), median (IQR) § | 205 (98-374) | 196 (110-394) | 208 (116-397) | .26 |
| IL-18 (pg/ml), median (IQR) § | 241 (193-286) | 246 (196-297) | 254 (209-313) | .002 |
| MCP-1 (pg/ml), median (IQR) § | 1390 (907-2090) | 1300 (794-2330) | 1605 (1030-2300) | .001 |
| MIP-1α (pg/ml), median (IQR) § | 17200 (11250-24950) | 17000 (10500-24100) | 18600 (12350-24750) | .05 |
| MIP-1β (pg/ml), median (IQR) § | 219000 (151000-298500) | 228000 (149000-303000) | 240000 (169000-316500) | .02 |
| MMP-2 (ng/ml), mean (SD) | 69.4 (19.5) | 70.2 (21.2) | 73.6 (18.8) | .002 |
| TNF-α (pg/ml), median (IQR) § | 2820 (1785-4245) | 2770 (1760-4020) | 2820 (1875-4150) | .52 |
| TNF-β (pg/ml), mean (SD) | 299 (135) | 302 (143) | 326 (133) | .004 |

CRP = C-reactive protein, IFN = Interferon, IL = Interleukin, MCP = Monocyte Chemotactic Protein, MIP = Macrophage Inflammatory Protein, MMP = Matrix Metalloproteinase, TNF = Tumor necrosis factor.

* Based on chi-square test for dichotomous and categorical variables and one-way ANOVA for continuous variables.

§ Kruskal-Wallis H test was used because of non-normal distribution.

TABLE 4

Association of Inflammatory Markers with presence of current depressive/anxiety disorder and with severity

|  | Current disorder | | | IDS | | BAI | |
|---|---|---|---|---|---|---|---|
| N = 1242 | OR | (95% CI) | p | β | p | β | p |
| IFN-γ | 0.94 | (0.79-1.11) | .48 | −.006 | .87 | .033 | .32 |
| IL-2 | 1.06 | (0.91-1.24) | .43 | .017 | .58 | .027 | .38 |
| IL-4 | 1.07 | (0.92-1.24) | .37 | .007 | .81 | −.024 | .40 |
| IL-6 | 1.07 | (0.89-1.28) | .50 | .054 | .14 | .091 | .01 |
| IL-8 | 1.35 | (1.16-1.59) | <.001 | .113 | <.001 | .109 | <.001 |
| IL-10 | 1.15 | (0.96-1.39) | .14 | .078 | .03 | .092 | .01 |
| IL-18 | 1.22 | (1.04-1.43) | .01 | .076 | .01 | .098 | .001 |
| MCP-1 | 1.17 | (0.99-1.39) | .07 | .134 | <.001 | .136 | <.001 |
| MIP-1α | 1.10 | (0.92-1.31) | .30 | .039 | .26 | .055 | .11 |
| MIP-1β | 1.19 | (1.00-1.42) | .05 | .073 | .04 | .092 | .007 |
| MMP2 | 1.15 | (0.98-1.36) | .09 | .103 | .001 | .130 | <.001 |
| TNF-α | 0.95 | (0.80-1.13) | .58 | −.005 | .88 | .021 | .53 |
| TNF-β | 1.15 | (0.98-1.35) | .09 | .069 | .03 | .109 | <.001 |

*based on logistic (no disorder = ref) and linear (IDS, BAI) regression analyses adjusted for age, sex, education and site.

In Table 5, double underline represents p<.05 and bold font represents p<.10.

Data revealed no consistent sex-interactions.

TABLE 6

Association* of inflammatory markers§ with depressive/anxiety disorder status
(N = 1242; no lifetime disorder = reference)

|  | Remittted disorder (N = 251) | | | Current disorder (N = 694) | | |
|---|---|---|---|---|---|---|
|  | OR | 95% CI | p | OR | 95% CI | p |
| Circulating inflammatory markers | | | | | | |
| CRP | 1.08 | 0.90-1.29 | .41 | 1.10 | 0.95-1.27 | .21 |
| IL-6 | 0.93 | 0.79-1.10 | .40 | 1.11 | 0.96-1.28 | .16 |
| TNF-α | 1.07 | 0.90-1.27 | .48 | 1.06 | 0.92-1.22 | .44 |

TABLE 5

Association* of inflammatory markers§ with depressive/anxiety disorder status
(N = 1242; no lifetime disorder = reference)

|  | Remittted disorder (N = 251) | | | Depression only (N=153) | | | Anxiety only (N = 217) | | | Comorbid disorder (N = 324) | | |
|---|---|---|---|---|---|---|---|---|---|---|---|---|
|  | OR | 95% CI | p | OR | 95% CI | p | OR | 95% CI | p | OR | 95% CI | p |
| Circulating inflammatory markers | | | | | | | | | | | | |
| CRP | 1.08 | 0.90-1.29 | .41 | 1.23 | 1.00-1.50 | .05 | 1.08 | 0.90-1.30 | .41 | 1.05 | 0.88-1.24 | .61 |
| IL-6 | 0.93 | 0.79-1.10 | .40 | 1.10 | 0.90-1.36 | .35 | 1.16 | 0.96-1.40 | .12 | 1.08 | 0.91-1.27 | .39 |
| TNF-α | 1.07 | 0.90-1.27 | .48 | 1.08 | 0.88-1.31 | .48 | 1.05 | 0.88-1.26 | .60 | 1.05 | 0.89-1.24 | .54 |
| LPS-stimulated inflammatory markers | | | | | | | | | | | | |
| IFN-γ | 0.82 | 0.67-1.01 | .06 | 0.77 | 0.61-0.99 | .04 | 0.98 | 0.79-1.22 | .89 | 1.01 | 0.83-1.24 | .91 |
| IL-2 | 1.07 | 0.89-1.29 | .49 | 1.05 | 0.84-1.30 | .67 | 1.02 | 0.84-1.24 | .88 | 1.11 | 0.92-1.33 | .27 |
| IL-4 | 1.14 | 0.95-1.37 | .15 | 1.12 | 0.91-1.37 | .29 | 1.13 | 0.94-1.35 | .21 | 1.01 | 0.85-1.19 | .93 |
| IL-6 | 0.95 | 0.76-1.18 | .62 | 0.94 | 0.73-1.21 | .61 | 1.12 | 0.88-1.43 | .36 | 1.11 | 0.89-1.39 | .35 |
| IL-8 | 1.36 | 1.13-1.64 | .001 | 1.37 | 1.10-1.71 | .005 | 1.25 | 1.03-1.54 | .03 | 1.43 | 1.18-1.72 | <.00 |
| IL-10 | 0.98 | 0.79-1.22 | .87 | 1.11 | 0.86-1.44 | .43 | 1.13 | 0.89-1.43 | .31 | 1.19 | 0.95-1.49 | .13 |
| IL-18 | 1.15 | 0.95-1.39 | .15 | 1.16 | 0.93-1.44 | .19 | 1.20 | 0.98-1.47 | .07 | 1.27 | 1.06-1.53 | .01 |
| MCP-1 | 1.02 | 0.83-1.25 | .88 | 1.13 | 0.89-1.43 | .32 | 1.20 | 0.97-1.49 | .10 | 1.17 | 0.96-1.43 | .11 |
| MIP-1α | 1.04 | 0.84-1.28 | .72 | 1.11 | 0.86-1.42 | .43 | 1.07 | 0.85-1.34 | .55 | 1.11 | 0.90-1.38 | .31 |
| MIP-1β | 1.05 | 0.85-1.30 | .66 | 1.17 | 0.91-1.49 | .22 | 1.17 | 0.93-1.47 | .18 | 1.21 | 0.98-1.50 | .07 |
| MMP2 | 1.07 | 0.88-1.31 | .50 | 1.09 | 0.86-1.37 | .48 | 1.15 | 0.93-1.42 | .20 | 1.19 | 0.98-1.45 | .08 |
| TNF-α | 0.91 | 0.74-1.11 | .35 | 0.84 | 0.66-1.06 | .15 | 0.99 | 0.79-1.23 | .91 | 1.00 | 0.81-1.23 | .99 |
| TNF-β | 1.04 | 0.85-1.27 | .72 | 1.13 | 0.90-1.41 | .30 | 1.14 | 0.93-1.40 | .21 | 1.17 | 0.97-1.41 | .10 |
| LPS summary measures± | | | | | | | | | | | | |
| LPS-total | 0.84 | 0.66-1.06 | .15 | 1.01 | 0.99-1.04 | .40 | 1.02 | 0.99-1.04 | .14 | 1.02 | 1.00-1.05 | .05 |
| LPS-index | 1.13 | 0.90-1.41 | .30 | 1.04 | 0.97-1.11 | .29 | 1.05 | 0.98-1.12 | .15 | 1.04 | 0.98-1.10 | .16 |

CRP = C-reactive protein, IFN = Interferon, IL = Interleukin, MCP = Monocyte Chemotactic Protein, MIP = Macrophage Inflammatory Protein, MMP = Matrix Metalloproteinase, TNF = Tumor necrosis factor.

*Based on multinomial logistic regression analyses with inflammatory markers as predictors and disorder status as outcome (no lifetime disorder = reference group) adjusted for laboratory site, sex, age and years of education.

§All markers were standardized: (value − mean)/SD; because of non-normal distributions standardization was performed after ln-transformation to normalize distributions for all markers except MMP2 and TNF-β (which were already normally distributed).

±LPS-total: sum of all standardized LPS markers; LPS-index: number of LPS markers in highest quartile.

TABLE 6-continued

Association* of inflammatory markers§ with depressive/anxiety disorder status
(N = 1242; no lifetime disorder = reference)

| | Remittted disorder (N = 251) | | | Current disorder (N = 694) | | |
|---|---|---|---|---|---|---|
| | OR | 95% CI | p | OR | 95% CI | p |
| LPS-stimulated inflammatory markers | | | | | | |
| IFN-γ | 0.82 | 0.67-1.01 | .06 | 0.94 | 0.79-1.11 | .48 |
| IL-2 | 1.07 | 0.89-1.29 | .49 | 1.06 | 0.91-1.24 | .43 |
| IL-4 | 1.14 | 0.95-1.37 | .15 | 1.07 | 0.92-1.24 | .37 |
| IL-6 | 0.95 | 0.76-1.18 | .62 | 1.07 | 0.89-1.28 | .50 |
| IL-8 | 1.36 | 1.13-1.64 | .001 | 1.35 | 1.16-1.59 | <.001 |
| IL-10 | 0.98 | 0.79-1.22 | .87 | 1.15 | 0.96-1.39 | .14 |
| IL-18 | 1.15 | 0.95-1.39 | .15 | 1.22 | 1.04-1.43 | .01 |
| MCP-1 | 1.02 | 0.83-1.25 | .88 | 1.17 | 0.99-1.39 | .07 |
| MIP-1α | 1.04 | 0.84-1.28 | .72 | 1.10 | 0.92-1.31 | .30 |
| MIP-1β | 1.05 | 0.85-1.30 | .66 | 1.19 | 1.00-1.42 | .056 |
| MMP2 | 1.07 | 0.88-1.31 | .50 | 1.15 | 0.98-1.36 | .09 |
| TNF-α | 0.91 | 0.74-1.11 | .35 | 0.95 | 0.80-1.13 | .58 |
| TNF-β | 1.04 | 0.85-1.27 | .72 | 1.15 | 0.98-1.35 | .09 |
| LPS summary measures± | | | | | | |
| LPS-total | 1.01 | 0.99-1.03 | .50 | 1.02 | 1.00-1.04 | .057 |
| LPS-index | 1.03 | 0.98-1.10 | .23 | 1.04 | 0.99-1.10 | .10 |

CRP = C-reactive protein, EFN = Interferon, EL = Interleukin, MCP = Monocyte Chemotactic Protein, MEP = Macrophage Inflammatory Protein, MMP = Matrix Metalloproteinase, TNF = Tumor necrosis factor.
*Based on multinomial logistic regression analyses with inflammatory markers as predictors and disorder status as outcome (no lifetime disorder = reference group) adjusted for laboratory site, sex, age and years of education.
§All markers were standardized: (value − mean)/SD; because of non-normal distributions standardization was performed after ln-transformation to normalize distributions for all markers except MMP2 and TNF-β (which were already normally distributed).
±LPS-total: sum of all standardized LPS markers; LPS-index: number of LPS markers in highest quartile.

In Table 6, double underline represents p<.05 and bold font represents p<.10.
Spearman's rho LPS-total–LPS-index=0.92

TABLE 7

Association* of inflammatory markers§ with depression and anxiety severity

| | Depression severity (IDS) N = 1228 | | Anxiety severity (BAI)± N = 1230 | | Depression severity (IDS) N = 1228 | | Anxiety severity (BAI)± N = 1230 | |
|---|---|---|---|---|---|---|---|---|
| | β | p | β | β | β | p | β | p |
| Circulating inflammatory markers | | | | | | | | |
| CRP | .044 | .12 | .030 | .29 | −.009 | .76 | −.016 | .60 |
| IL-6 | .076 | .007 | .052 | .06 | .049 | .09 | .027 | .34 |
| TNF-α | 0.49 | .08 | .029 | .30 | .039 | .15 | .021 | .43 |
| LPS-stimulated inflammatory markers | | | | | | | | |
| IFN-γ | −.006 | .87 | .033 | .32 | −.001 | .97 | .042 | .20 |
| IL-2 | .017 | .58 | .027 | .38 | .012 | .70 | .022 | .46 |
| IL-4 | .007 | .81 | −.024 | .40 | .006 | .84 | −.024 | .39 |
| IL-6 | .054 | .14 | .091 | .01 | .014 | .69 | .053 | .13 |
| IL-8 | .113 | <.001 | .109 | <.001 | .073 | .02 | .067 | .03 |
| IL-10 | .078 | .03 | .092 | .01 | .048 | .19 | .055 | .13 |
| IL-18 | .076 | .01 | .098 | .001 | .047 | .12 | .070 | .02 |
| MCP-1 | .134 | <.001 | .136 | <.001 | .092 | .006 | .091 | .007 |
| MIP-1α | .039 | .26 | .055 | .11 | .012 | .73 | .030 | .38 |
| MIP-1β | .073 | .04 | .092 | .007 | .039 | .27 | .056 | .11 |
| MMP2 | .103 | .001 | .130 | <.001 | .081 | .01 | .109 | .001 |
| TNF-α | −.005 | .88 | .021 | .53 | .005 | .88 | .042 | .21 |
| TNF-β | .069 | .03 | .109 | <.001 | 0.57 | .07 | .098 | .002 |
| LPS summary measures# | | | | | | | | |
| LPS-total | .091 | .01 | .114 | .001 | .061 | .09 | .086 | .02 |
| LPS-index | .070 | .02 | .108 | <.001 | .045 | .13 | .083 | .005 |

CRP = C-reactive protein, EFN = Interferon, IL = Interleukin, MCP = Monocyte Chemotactic Protein, MIP = Macrophage Inflammatory Protein, MMP = Matrix Metalloproteinase, TNF = Tumor necrosis factor.
*Based on linear regression analyses with inflammatory markers as predictors and severity as outcome adjusted for laboratory site, sex, age and years of education (basic adjustment) and additionally for current smoking and BMI (lifestyle adjustment).
§All markers were standardized: (value − mean)/SD; because of non-normal distributions standardization was performed after ln-transformation to normalize distributions for all markers except MMP2 and TNF-β (which were already normally distributed).
±Square root of BAI was taken to normalize distribution.
LPS-total: sum of all standardized LPS markers; number of LPS markers in highest quartile.

In Table 7, double underline represents p<.05 and bold font represents p<.10.
 Spearman's rho IDS-BAI=0.83
 Pearson's r IDS-SQRT(BAI+1)=0.82

TABLE 8

Association* of inflammatory markers§ with depression and anxiety severity

| | Depression severity (IDS) N = 687 | | Anxiety severity (BAI)± N = 688 | | Symptoms duration N = 678 | | Age of Onset N = 681 | |
|---|---|---|---|---|---|---|---|---|
| | β | p | β | β | β | p | β | p |
| Circulating inflammatory markers | | | | | | | | |
| CRP | .017 | .66 | .002 | .97 | −.042 | .28 | .047 | .21 |
| IL-6 | .082 | .03 | .052 | .17 | −.020 | .62 | .020 | .60 |
| TNF-α | .075 | .05 | .066 | .08 | −.008 | .83 | .028 | .44 |
| LPS-stimulated inflammatory markers | | | | | | | | |
| IFN-γ | .005 | .90 | .078 | .07 | −.006 | .88 | −.018 | .67 |
| IL-2 | .007 | .86 | .014 | .73 | −.026 | .52 | .032 | .41 |
| IL-4 | .003 | .94 | −.054 | .16 | −.052 | .19 | .051 | .17 |
| IL-6 | .055 | .23 | .133 | .003 | .014 | .77 | −.015 | .74 |
| IL-8 | .085 | .04 | .098 | .02 | .031 | .46 | .032 | .41 |
| IL-10 | .059 | .23 | .143 | .003 | −.020 | .68 | −.014 | .77 |
| IL-18 | .043 | .28 | .076 | .05 | −.019 | .64 | .039 | .30 |
| MCP-1 | .121 | .004 | .129 | .002 | .044 | .31 | .018 | .66 |
| MIP-1α | .050 | .25 | .102 | .02 | −.029 | .52 | .026 | .54 |
| MIP-1β | .064 | .14 | .124 | .004 | −.019 | .66 | −.009 | .83 |
| MMP2 | .106 | .01 | .144 | <.00 | −.004 | .93 | −.012 | .75 |
| TNF-α | .016 | .71 | 0.77 | .07 | .018 | .41 | −.006 | .89 |
| TNF-β | .028 | .50 | .090 | .03 | −.035 | .40 | −.007 | .85 |
| LPS summary measures# | | | | | | | | |
| LPS-total | .071 | .11 | .126 | .004 | −.018 | .69 | .012 | .77 |
| LPS-index | .054 | .17 | .122 | .002 | −.016 | .69 | −.007 | .85 |

CRP = C-reactive protein, EFN = Interferon, IL = Interleukin, MCP = Monocyte Chemotactic Protein, MIP = Macrophage Inflammatory Protein, MMP = Matrix Metalloproteinase, TNF = Tumor necrosis factor.
*Based on linear regression analyses with inflammatory markers as predictors and severity as outcome adjusted for laboratory site, sex, age and years of education (basic adjustment) and additionally for current smoking and BMI (lifestyle adjustment).
§All markers were standardized: (value − mean)/SD; because of non-normal distributions standardization was performed after ln-transformation to normalize distributions for all markers except MMP2 and TNF-β (which were already normally distributed).
±Square root of BAI was taken to normalize distribution. #LPS-total: sum of all standardized LPS markers; number of LPS markers in highest quartile.

In Table 8, double underline represents p<.05 and bold font represents p<.10.
 Spearman's rho IDS-BAI=0.67
 Pearson's r IDS-SQRT(BAI+1)=0.69
 Spearman's rho LPS-total–LPS-index=0.91

TABLE 9

Association* of inflammatory markers with antidepressant use in subsample of persons with a current depressive/anxiety disorder (n = 694).
Antidepressent use (no = reference)

| | SSRI (n = 173) | | | SNRI (n = 41) | | | TCA/TeCA (n = 50) | | | Any (n = 264) | | |
|---|---|---|---|---|---|---|---|---|---|---|---|---|
| | OR | 95% CI | p | OR | 95% CI | p | OR | 95% CI | p | OR | 95% CI | p |
| Circulating inflammatory markers | | | | | | | | | | | | |
| CRP | 1.10 | 0.91- | .32 | 1.37 | 0.98-1.91 | .06 | 1.73 | 1.27-2.35 | .001 | 1.23 | 1.05-1.44 | .01 |
| IL-6 | 1.13 | 0.93- | .21 | 1.31 | 0.89-1.93 | .16 | 0.98 | 0.73-1.30 | .86 | 1.12 | 0.95-1.31 | .19 |
| TNF-α | 1.06 | 0.89- | .50 | 0.98 | 0.70-1.38 | .92 | 1.03 | 0.77-1.37 | .86 | 1.05 | 0.90-1.22 | .57 |
| LPS-stimulated inflammatory markers | | | | | | | | | | | | |
| IFN-γ | 1.10 | 0.88-1.38 | .42 | 1.27 | 0.90-1.81 | .18 | 1.25 | 0.84-1.88 | .27 | 1.16 | 0.95-1.40 | .15 |
| IL-2 | 1.03 | 0.85-1.25 | .77 | 1.06 | 0.76-1.49 | .74 | 0.92 | 0.67-1.27 | .62 | 1.01 | 0.86-1.20 | .88 |
| IL-4 | 0.97 | 0.81-1.17 | .78 | 1.04 | 0.74-1.47 | .82 | 0.86 | 0.63-1.16 | .32 | 0.96 | 0.82-1.13 | .96 |
| IL-6 | 1.21 | 0.94-1.55 | .13 | 1.22 | 0.84-1.76 | .30 | 1.01 | 0.67-1.53 | .95 | 1.17 | 0.95-1.45 | .14 |
| IL-8 | 1.00 | 0.80-1.23 | .97 | 1.15 | 0.82-1.62 | .42 | 1.45 | 0.99-2.11 | .06 | 1.09 | 0.90-1.30 | .38 |
| IL-10 | 1.20 | 0.94-1.54 | .14 | 1.23 | 0.83-1.82 | .31 | 0.97 | 0.64-1.45 | .86 | 1.16 | 0.94-1.43 | .16 |
| IL-18 | 1.12 | 0.92-1.37 | .25 | 1.35 | 0.96-1.91 | .08 | 1.03 | 0.74-1.45 | .85 | 1.14 | 0.96-1.36 | .13 |

TABLE 9-continued

Association* of inflammatory markers with antidepressant use in subsample of
persons with a current depressive/anxiety disorder (n = 694).
Antidepressant use (no = reference)

| | SSRI (n = 173) | | | SNRI (n = 41) | | | TCA/TeCA (n = 50) | | | Any (n = 264) | | |
|---|---|---|---|---|---|---|---|---|---|---|---|---|
| | OR | 95% CI | p | OR | 95% CI | p | OR | 95% CI | p | OR | 95% CI | p |
| MCP-1 | 1.18 | 0.95-1.46 | .14 | 1.32 | 0.94-1.87 | .11 | 1.32 | 0.91-1.92 | .14 | <u>1.23</u> | <u>1.02-1.48</u> | <u>.03</u> |
| MIP-1α | 1.05 | 0.83-1.32 | .71 | 1.39 | 0.95-2.03 | .09 | 1.07 | 0.71-1.62 | .75 | 1.11 | 0.91-1.48 | .30 |
| MIP-1β | 1.19 | 0.94-1.50 | .15 | <u>1.62</u> | <u>1.11-2.37</u> | <u>.01</u> | 0.89 | 0.60-1.31 | .55 | 1.20 | 0.98-1.46 | .08 |
| MMP2 | <u>1.26</u> | <u>1.02-1.55</u> | <u>.03</u> | 1.17 | 0.86-1.59 | .31 | 1.12 | 0.78-1.61 | .53 | <u>1.22</u> | <u>1.02-1.45</u> | <u>.03</u> |
| TNF-α | 1.05 | 0.84-1.30 | .69 | 1.34 | 0.93-1.92 | .12 | 1.00 | 0.69-1.46 | .99 | 1.09 | 0.90-1.32 | .37 |
| TNF-β | 1.14 | 0.94-1.40 | .19 | 1.25 | 0.89-1.75 | .20 | 0.99 | 0.70-1.39 | .95 | 1.13 | 0.95-1.35 | .16 |
| | | | | | LPS summary measures# | | | | | | | |
| LPS-total | 1.02 | 0.99-1.04 | .17 | 1.03 | 1.00-1.07 | .09 | 1.01 | 0.97-1.05 | .72 | 1.02 | 1.00-1.04 | .08 |
| LPS-index | 1.05 | 0.99-1.11 | .14 | 1.04 | 0.94-1.16 | .46 | 1.03 | 0.93-1.14 | .58 | 1.04 | 0.99-1.10 | .13 |

CRP = C-reactive protein, IFN = Interferon, IL = Interleukin, MCP = Monocyte Chemotactic Protein, MIP = Macrophage Inflammatory Protein, MMP = Matrix Metalloproteinase, TNF = Tumor necrosis factor.
*Based on linear and multinomial logistic regression analyses with inflammatory markers as predictors and severity as outcome adjusted for laboratory site, sex, age and years of education.
§All markers were standardized: (value − mean)/SD; because of non-normal distributions standardization was performed after ln-transformation to normalize distributions for all markers except MMP2 and TNF-β (which were already normally distributed).
LPS-total: sum of all standardized LPS markers; number of LPS markers in highest quartile.

In Table 9, double underline represents p<.05 and bold font represents p<.10.

The invention claimed is:

1. A method of diagnosing and treating depression or anxiety disorder or predisposition in an individual thereto, comprising:
   (a) obtaining a biological sample from the individual and quantifying the amounts of biomarkers in the biological sample, wherein the biomarkers comprise at least two biomarkers selected from the group consisting of interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-1β), Matrix Metalloproteinase 2 (MMP-2), Tumor Necrosis Factor beta (TNF-β), Interleukin 4 (IL-4), Interferon gamma (IFN-γ);
   (b) quantifying the amounts of the biomarkers in a control population to generate a reference standard wherein the control population comprises normal subjects;
   (c) comparing the amounts of the biomarkers in the biological sample with the amounts present in the reference standard; and
   (d) diagnosing the individual as having depression or anxiety disorder when the amount of the biomarkers in the biological sample is greater than the amount of biomarkers in the reference standard; and
   (e) administering a therapeutically effective amount of an antidepressant to the individual diagnosed as having depression or a therapeutically effective amount of an anxiolytic drug to the individual diagnosed as having anxiety disorder;
   wherein the quantifying is performed by measuring the concentration of the analyte biomarker in each sample by one or more methods selected from SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC or other LC or LC-MS-based technique, by an immunological method, or by a biosensor or a microanalytical, microengineered, microseparation or immunochromatography system.

2. The method of claim 1, wherein the biomarkers further comprise one or more biomarkers selected from the group consisting of C-reactive protein CMP, Interleukin 6 (IL-6) and Tumor Necrosis Factor alpha (TNF-α).

3. The method of claim 1, wherein the biological sample is cerebrospinal fluid, whole blood, blood serum, plasma, urine, saliva, or other bodily fluid, or breath, condensed breath, or an extract or purification therefrom, or dilution thereof.

4. The method of claim 1, wherein the individual is diagnosed as having depression and the treating comprises administering to the individual an antidepressant.

5. The method of claim 1, wherein the antidepressant is selected from the group consisting of a selective serotonin reuptake inhibitor, a serotonin-norepinephrine reuptake inhibitor, a norepinephrine and dopamine reuptake inhibitor, a tetracyclic antidepressant, a tricyclic antidepressant, and a monoamine oxidase inhibitor.

6. The method of claim 1, wherein the individual is diagnosed as having anxiety disorder and the treating comprises administering to the individual an anxiolytic drug.

7. The method of claim 1, wherein the anxiolytic drug is selected from the group consisting of a serotonin reuptake inhibitor, a serotonin-norepinephrine reuptake inhibitor, a benzodiazepine drug, and a tricyclic antidepressant.

8. A method of monitoring efficacy of a therapy for depression or anxiety disorder in a subject undergoing the therapy, comprising:
   (a) administering to the subject an antidepressant or an anxiolytic,
   (b) obtaining a biological sample from the subject and quantifying the amounts of biomarkers in the biological sample, wherein the biomarkers comprise at least two biomarkers selected from the group consisting of interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-β), Matrix Metalloproteinase 2 (MMP-2), Tumor Necrosis Factor beta (TNF-β), Interleukin 4 (IL-4), Interferon gamma (IFN-γ);
   (c) quantifying the amounts of the biomarkers in a reference standard wherein the reference standard was obtained from the subject prior to the therapy;

(d) comparing the amounts of the biomarkers in the biological sample with the amounts present in the reference standard; and (e) determining that the therapy is effective when the amounts of the biomarkers in the biological sample obtained from the subject is less than the amounts of the biomarkers present in the reference standard;

wherein the quantifying is performed by measuring the concentration of the analyte biomarker in each sample by one or more methods selected from SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC or other LC or LC-MS-based technique, by an immunological method, or by a biosensor or a microanalytical, microengineered, microseparation or immunochromatography system.

9. The method of claim 8, wherein the biomarkers are quantified on samples taken on two or more occasions from the individual.

10. The method of claim 9, wherein one of the two or more occasions is prior to commencement of therapy and one of the two or more occasions is after commencement of therapy.

11. The method of claim 9, wherein an effect the therapy has on an individual is determined based a change in the amount of the biomarkers in samples taken on two or more occasions.

12. The method of claim 10, wherein the occasion after commencement of therapy is following therapy.

13. The method of claim 9, wherein samples are taken at intervals over the remaining life, or a part thereof, of the subject.

14. The method of claim 8, wherein quantifying is performed by measuring the concentration of the analyte biomarker in each sample.

15. The method of claim 8, wherein the quantifying is performed by one or more methods selected from SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC or other LC or LC-MS-based technique.

16. The method of claim 8, wherein the quantifying is performed using an immunological method.

17. The method of claim 8, wherein the quantifying is performed using a biosensor or a microanalytical, microengineered, microseparation or immunochromatography system.

18. The method of claim 8, wherein the biological sample is cerebrospinal fluid, whole blood, blood serum, plasma, urine, saliva, or other bodily fluid, or breath, condensed breath, or an extract or purification therefrom, or dilution thereof.

19. The method of claim 8, wherein the biomarkers further comprise one or more biomarkers selected from the group consisting of C-reactive protein (CRP), Interleukin 6 (IL-6) and Tumor Necrosis Factor alpha (TNF-α).

20. A method comprising:

(a) obtaining a reference standard from a subject;

(b) administering to the subject an antidepressant or an anxiolytic, (c) obtaining a biological sample from the subject and quantifying the amounts of biomarkers in the biological sample, wherein the biomarkers comprise at least two biomarkers selected from the group consisting of interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-β), Matrix Metalloproteinase 2 (MMP-2), Tumor Necrosis Factor beta (TNF-β), Interleukin 4 (IL-4), Interferon gamma (IFN-γ); and (d) quantifying the amounts of the biomarkers in the reference standard;

wherein the quantifying is performed by measuring the concentration of the analyte biomarker in each sample by one or more methods selected from SELDI (-TOF), MALDI (-TOF), a 1-D gelbased analysis, a 2-D gel-based analysis, Mass spec (MS), reverse phase (RP) LC, size permeation (gel filtration), ion exchange, affinity, HPLC, UPLC or other LC or LC-MS-based technique, by an immunological method, or by a biosensor or a microanalytical, microengineered, microseparation or immunochromatography system.

21. The method of claim 20, wherein the biomarkers further comprise one or more biomarkers selected from the group consisting of C-reactive protein (CRP), Interleukin 6 (IL-6) and Tumor Necrosis Factor alpha (TNF-α).

22. The method of claim 20, wherein the biomarkers comprise interleukin 10 (IL-10), Interleukin 18 (IL-18), Interleukin 2 (IL-2), Interleukin 8 (IL-8), Monocyte Chemotactic Protein 1 (MCP-1), Macrophage Inflammatory Protein 1 alpha (MIP-1α), Macrophage Inflammatory Protein 1 beta (MIP-β), Matrix Metalloproteinase 2 (MMP-2), Tumor Necrosis Factor beta (TNF-β), Interleukin 4 (IL-4), Interferon gamma (IFN-γ), Interleukin 6 (IL-6) and Tumor Necrosis Factor alpha (TNF-α).

23. The method of claim 22, wherein the biomarkers further comprise C-reactive protein (CRP).

\* \* \* \* \*

UNITED STATES PATENT AND TRADEMARK OFFICE
CERTIFICATE OF CORRECTION

PATENT NO. : 10,101,338 B2
APPLICATION NO. : 14/570076
DATED : October 16, 2018
INVENTOR(S) : Bahn et al.

It is certified that error appears in the above-identified patent and that said Letters Patent is hereby corrected as shown below:

In the Claims

Column 35, Line 57, Claim 1 please delete "each sample" and insert --the biological sample and the reference standard--

Column 36, Line 24, Claim 2 please delete "CMP" and insert --(CRP)--

Column 36, Line 32, Claim 4 please delete "treating" and insert --administering--
Column 36, Line 33, Claim 4 please delete "an" and insert --the--

Column 36, Line 41, Claim 6 please delete "treating" and insert --administering--
Column 36, Line 42, Claim 6 please delete "an" and insert --the--

Column 37, Line 9, Claim 8 please delete "each sample" and insert --the biological sample and the reference standard--

Column 37, Line 20, Claim 9 please delete "individual" and insert --subject--

Column 37, Line 36, Claim 14 please delete "each sample" and insert --the biological sample and the reference standard--

Column 38, Line 20, Claim 20 please delete "(MIP-β)," and insert --(MIP-1β),--
Column 38, Line 26, Claim 20 please delete "each sample" and insert --the biological sample and the reference standard--

Column 38, Line 44, Claim 22 please delete "(MIP-β)," and insert --(MIP-1β),--

Signed and Sealed this
Fifth Day of May, 2020

Andrei Iancu
*Director of the United States Patent and Trademark Office*